(12) United States Patent
Ding

(10) Patent No.: US 9,655,751 B2
(45) Date of Patent: May 23, 2017

(54) KITS INCLUDING IMPLANTABLE MEDICAL DEVICES AND ANTIOXIDANTS

(71) Applicant: Abbott Cardiovascular Systems Inc., Santa Clara, CA (US)

(72) Inventor: Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 307 days.

(21) Appl. No.: 13/759,898

(22) Filed: Feb. 5, 2013

(65) Prior Publication Data

US 2013/0150953 A1    Jun. 13, 2013

Related U.S. Application Data

(60) Division of application No. 12/485,756, filed on Jun. 16, 2009, now Pat. No. 8,394,446, which is a continuation-in-part of application No. 11/528,891, filed on Sep. 27, 2006, now abandoned, and a continuation-in-part of application No. 11/189,216, filed on Jul. 25, 2005, now Pat. No. 7,785,647.

(51) Int. Cl.
| | |
|---|---|
| *B65D 77/04* | (2006.01) |
| *A61F 2/82* | (2013.01) |
| *A61L 31/10* | (2006.01) |
| *A61L 31/14* | (2006.01) |
| *B65B 55/00* | (2006.01) |
| *C08K 5/13* | (2006.01) |
| *B65D 1/00* | (2006.01) |
| *B65D 3/00* | (2006.01) |

(52) U.S. Cl.
CPC ............. *A61F 2/82* (2013.01); *A61L 31/10* (2013.01); *A61L 31/143* (2013.01); *B65B 55/00* (2013.01); *B65D 1/00* (2013.01); *C08K 5/13* (2013.01); *B65D 3/00* (2013.01); *B65D 77/04* (2013.01)

(58) Field of Classification Search
USPC ................................. 427/2.24, 2.1; 206/438
See application file for complete search history.

(56) References Cited

U.S. PATENT DOCUMENTS

| | | | |
|---|---|---|---|
| 3,429,717 A * | 2/1969 | Cook | ............................ 426/127 |
| 3,993,622 A | 11/1976 | Brunetti | |
| 4,401,804 A | 8/1983 | Wooten et al. | |
| 5,006,281 A | 4/1991 | Rubin et al. | |
| 5,288,711 A | 2/1994 | Mitchell et al. | |
| 5,344,425 A | 9/1994 | Sawyer | |

(Continued)

FOREIGN PATENT DOCUMENTS

| | | |
|---|---|---|
| JP | 2003-253031 | 9/2003 |
| WO | WO 98/41559 | 9/1998 |

(Continued)

OTHER PUBLICATIONS

International Search Report for PCT/US2006/027050, mailed Apr. 16, 2007, 9 pgs.

(Continued)

*Primary Examiner* — Dah-Wei D Yuan
*Assistant Examiner* — Andrew Bowman
(74) *Attorney, Agent, or Firm* — Squire Patton Boggs (US) LLP

(57) ABSTRACT

Methods of incorporating an antioxidant into a medical device including a polymer are described, and methods of packaging medical devices.

17 Claims, 3 Drawing Sheets

(56) References Cited

U.S. PATENT DOCUMENTS

| | | | |
|---|---|---|---|
| 5,527,337 A | 6/1996 | Stack et al. | |
| 5,539,081 A | 7/1996 | Gruber et al. | |
| 5,581,387 A | 12/1996 | Cahill et al. | |
| 5,618,866 A | 4/1997 | Prabhu et al. | |
| 5,992,000 A | 11/1999 | Humphrey et al. | |
| 6,037,022 A | 3/2000 | Adur et al. | |
| 6,065,597 A | 5/2000 | Pettersson et al. | |
| 6,309,383 B1 | 10/2001 | Campbell et al. | |
| 6,485,950 B1 | 11/2002 | Kumar et al. | |
| 6,608,187 B2 | 8/2003 | Nelson et al. | |
| 6,727,300 B2 | 4/2004 | Sassi | |
| 6,746,622 B2 | 6/2004 | Yang et al. | |
| 6,875,400 B2 | 4/2005 | Speer | |
| 6,949,254 B2 | 9/2005 | Gen | |
| 7,022,258 B2 | 4/2006 | Yang et al. | |
| 7,704,518 B2 | 4/2010 | Tamarkin et al. | |
| 7,785,647 B2 | 8/2010 | Ding | |
| 8,128,688 B2 | 3/2012 | Ding et al. | |
| 8,207,240 B2 | 6/2012 | Lambert et al. | |
| 8,394,446 B2 | 3/2013 | Ding | |
| 2002/0015542 A1* | 2/2002 | Bradley | 383/211 |
| 2002/0022144 A1 | 2/2002 | Yang et al. | |
| 2002/0055769 A1 | 5/2002 | Wang | |
| 2002/0153511 A1 | 10/2002 | Cotterman et al. | |
| 2003/0083646 A1 | 5/2003 | Sirhan et al. | |
| 2003/0144145 A1 | 7/2003 | Yang et al. | |
| 2003/0189192 A1 | 10/2003 | Girelli et al. | |
| 2003/0204239 A1 | 10/2003 | Carlyle et al. | |
| 2003/0215564 A1 | 11/2003 | Heller et al. | |
| 2003/0216806 A1 | 11/2003 | Togawa et al. | |
| 2004/0033269 A1 | 2/2004 | Hei et al. | |
| 2004/0116332 A1 | 6/2004 | Ornberg et al. | |
| 2004/0220660 A1 | 11/2004 | Shanley et al. | |
| 2005/0004663 A1* | 1/2005 | Llanos et al. | 623/1.46 |
| 2005/0037048 A1 | 2/2005 | Song | |
| 2005/0268573 A1 | 12/2005 | Yan | |
| 2007/0198080 A1 | 8/2007 | Ding | |
| 2009/0319031 A1 | 12/2009 | Wang et al. | |
| 2010/0036047 A1 | 2/2010 | Janowicz et al. | |
| 2010/0300903 A1 | 12/2010 | Ding | |
| 2010/0300917 A1 | 12/2010 | Ding | |

FOREIGN PATENT DOCUMENTS

| | | |
|---|---|---|
| WO | WO 01/90202 | 11/2001 |
| WO | WO 03/053171 | 7/2003 |
| WO | WO 2004/050795 | 6/2004 |
| WO | WO 2005/016399 | 2/2005 |

OTHER PUBLICATIONS

Mayzo "BNX® MD-1024 Antioxidant & Metal Deactivator", product data sheet, 3 pgs. (2005).

Romanova et al., "Study of antioxidant effect of apigenin, luteolin and quercetin by DNA protective method", Neoplasma 48(2) pp. 104-107 (2001).

Ethylene oxide, Sterilization microbiology, Wikipedia, downloaded from: http://en.wikipedia.org/wiki/Sterilization_(microbiology), Apr. 24, 2012, 1 pg.

Lazada, Water Dessicant Pack (Anti-Fog), 2013, Lazada.com, www.lazada.com.my/Watershot-Desiccant-Pack-Anti-Fog-451390.html.

"TechBarrier S", Mitsubishi Plastics, Feb. 8, 2015, www.techbarrier.com/type/category05/index.html.

"Introduction to Volatile Organic Compounds (VOCs)", Home Institute, Feb. 8, 2015, http://www.homeinstitute.com/introduction-to-volatile-organic-compounds-vocs.html.

"Discoloration of Polyurethane Foam", FXI Industries, Feb. 8, 2015, http://fxi.com/assets/pdf/up_06_quality/Discoloration_info_Sheet_-_111010.pdf.

"Volatile Organic Compounds in your home", Minnesota Dept. of Health, Feb. 8, 2015, http://www.health.state.mn.us/divs/eh/indoorair/voc.

Request for Continued Examination and Response to Final Rejection in U.S. Appl. No. 13/760,540, filed Apr. 15, 2016; 9 pages.

Advisory Action in U.S. Appl. No. 13/760,540, mailed on Apr. 8, 2016; 4 pages.

Response to Final Rejection in U.S. Appl. No. 13/760,540, filed Mar. 18, 2016; 10 pages.

Final Rejection in U.S. Appl. No. 13/760,540, mailed Jan. 15, 2016; 20 pages.

Request for Continued Examination and Response to Final Rejection in U.S. Appl. No. 13/760,540, filed Jul. 13, 2015; 16 pages.

Notice of Appeal in U.S. Appl. No. 13/760,540, filed May 13, 2015, 2 pages.

Non-Final Rejection in U.S. Appl. No. 13/760,540, mailed Feb. 13, 2015, 18 pages.

Appeal Brief in U.S. Appl. No. 13/760,540, filed Sep. 30, 2014, 25 pages.

Advisory Action in U.S. Appl. No. 13/760,540, mailed on Jun. 13, 2014; 3 pages.

Response to Final Rejection in U.S. Appl. No. 13/760,540, filed May 28, 2015, 11 pages.

Final Rejection in U.S. Appl. No. 13/760,540, mailed on Mar. 28, 2014, 14 pages.

Response to Non-Final Rejection in U.S. Appl. No. 13/760,540, filed Jan. 15, 2014, 13 pages.

Non-Final Rejection in U.S. Appl. No. 13/760,540, mailed on Oct. 15, 2013, 13 pages.

Response to Restriction Requirement in U.S. Appl. No. 13/760,540, filed May 30, 2013; 2 pages.

Restriction Requirement in U.S. Appl. No. 13/760,540, mailed on Apr. 30, 2013; 6 pages.

Non-Final Rejection in U.S. Appl. No. 12/851,414, mailed on Feb. 3, 2011; 8 pages.

Response to Non-Final Rejection in U.S. Appl. No. 12/851,414, filed Jun. 3, 2011; 8 pages.

Final Rejection in U.S. Appl. No. 12/851,414, mailed on Aug. 26, 2011; 9 pages.

Request for Continued Examination and Response to Final Rejection in U.S. Appl. No. 12/851,414, filed Nov. 22, 2011; 7 pages.

Non-Final Rejection in U.S. Appl. No. 12/851,414, mailed on Feb. 1, 2013; 9 pages.

Response to Non-Final Rejection in U.S. Appl. No. 12/851,414, filed May 1, 2013; 7 pages.

Final Rejection in U.S. Appl. No. 12/851,414, mailed on Aug. 23, 2013; 10 pages.

Response to Final Rejection in U.S. Appl. No. 12/851,414, filed on Oct. 23, 2013; 9 pages.

Advisory Action in U.S. Appl. No. 12/851,414, mailed on Nov. 6, 2013; 3 pages.

Appeal Brief in U.S. Appl. No. 12/851,414, filed Jan. 21, 2014; 19 pages.

Examiner's Answer in U.S. Appl. No. 12/851,414, mailed on Jul. 1, 2014; 13 pages.

Reply Brief in U.S. Appl. No. 12/851,414, filed Sep. 2, 2014; 9 pages.

Patent Trial and Appeal Board Decision in U.S. Appl. No. 12/851,414, mailed on Apr. 28, 2016; 7 pages.

Appeal Brief in U.S. Appl. No. 12/851,420, filed Oct. 14, 2014; 146 pages.

Examiner's Answer in U.S. Appl. No. 12/851,420, mailed on Feb. 27, 2015; 9 pages.

Reply Brief in U.S. Appl. No. 12/851,420, filed Apr. 27, 2015; 7 pages.

* cited by examiner

KITS INCLUDING IMPLANTABLE MEDICAL DEVICES AND ANTIOXIDANTS

CROSS-REFERENCE TO RELATED APPLICATIONS

This application is a divisional application of copending U.S. application Ser. No. 12/485,756, filed on Jun. 16, 2009, published on Oct. 1, 2009, as U.S. Patent Application Publication No. 2009-0246253 A1, and issued as U.S. Pat. No. 8,394,446 B2on Mar. 12, 2013, which is a continuation-in-part of U.S. application Ser. No. 11/189,216, filed Jul. 25, 2005, published on Jan. 25, 2007, as U.S. Patent Application Publication No. 2007/0020380 A1, and issued on Aug. 31, 2010, as U.S. Pat. No. 7,785,647; and U.S. application Ser. No. 12/485,756 is a continuation-in-part of U.S. application Ser. No. 11/528,891, filed on Sep. 27, 2006, and published on Aug. 23, 2007, as U.S. Patent Application Publication No. 2007/0198080 A1, which is now abandoned. U.S. application Ser. Nos. 12/485,756 and 11/189,216 are hereby incorporated by reference herein as if fully set forth, including any drawings.

BACKGROUND OF THE INVENTION

1. Field of the Invention

This invention relates to the fields of chemistry, chemical engineering, and medical devices.

2. Description of the State of the Art

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies) was coronary by-pass surgery. While effective and having evolved to a relatively high degree of safety for such an invasive procedure, by-pass surgery still involves serious potential complications and in the best of cases, an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, failed to satisfactorily ameliorate another problem, restenosis, the re-clogging of the treated artery.

The next improvement, advanced in the mid-1980s, was use of a stent to scaffold the vessel wall in place after PTCA. This for all intents and purposes put an end to recoil but did not entirely resolve the issue of restenosis. That is, prior to the introduction of stents, restenosis occurred in from 30-50% of patients undergoing PTCA. Stenting reduced this to about 15-20%, much improved, but still more than desirable.

In 2003, drug-eluting stents or DESs were introduced. The drugs initially employed with the DES were cytostatic compounds, compounds that curtailed the proliferation of cells that resulted in restenosis. The occurrence of restenosis was thereby reduced to about 5-7%, a relatively acceptable figure. Today, the DES is the default industry standard for the treatment of atherosclerosis and is rapidly gaining favor for treatment of stenoses of blood vessels other than coronary arteries such as peripheral angioplasty of the superficial femoral artery.

The next generation of stents will be those designed to be biodegradable. Although bioerodable metals may be used, biodegradable polymers are often used for fabrication of a stent. However, there are potential shortcomings in the use of polymers as a material for implantable medical devices, such as stents. Polymers that biodegrade in the body may also degrade during the process of manufacturing, or during storage.

Methods of incorporating an antioxidant into a medical device that includes a polymer to reduce or limit the polymer degradation, and methods to enhance device shelf-life are needed. The present invention provides such methods.

SUMMARY OF THE INVENTION

Various embodiments of the present invention include methods of incorporating an antioxidant into an implantable medical device. The methods include, but are not necessarily limited to: providing an implantable medical device comprising a polymer, and exposing the device to a fluid comprising an antioxidant such that some of the antioxidant from the fluid is incorporated into the device. The fluid may be free of or substantially free of polymers and drugs. The fluid may comprise at least 10 ppm antioxidant.

Various embodiments of the present invention include methods of fabricating a polymeric stent are provided. Such methods include, but are not necessarily limited to: forming a polymeric tube, or providing a polymeric tube; cutting a stent pattern into the tube to form a polymeric stent; and exposing the polymeric stent or the polymeric tube to a fluid including an antioxidant. The exposure of the polymeric stent or the polymeric tube to the fluid including the antioxidant results in incorporation of some of the antioxidant into the polymeric stent or polymeric tube.

Various embodiments of the present invention include kits. The kits include, but are not necessarily limited to an implantable medical device comprising a polymer and optionally comprising an antioxidant, the device antioxidant; and a primary package with an interior, an interior surface and an exterior surface, the primary package comprising a second antioxidant, which may be the same as or different from the device antioxidant. The implantable medical device may be sealed inside the primary package, and the fluid filling the inside of the package and surrounding the device contains at least 0.001 µg/cm$^3$ antioxidant.

Various embodiments of the present invention include methods of packaging implantable medical devices. The methods include, but are not limited to: providing an implantable medical device; providing a package and an antioxidant or providing a package integrated with an antioxidant; placing the implantable medical device and the antioxidant in the package or placing the implantable medical device in the package integrated with the antioxidant; and sealing the implantable medical device and antioxidant in the package or sealing the implantable medical device in the package integrated with the antioxidant. The fluid filling the inside of the sealed package and surrounding the device may contain at least 0.001 µg/cm$^3$ antioxidant.

DETAILED DESCRIPTION OF THE INVENTION

Figure 1:
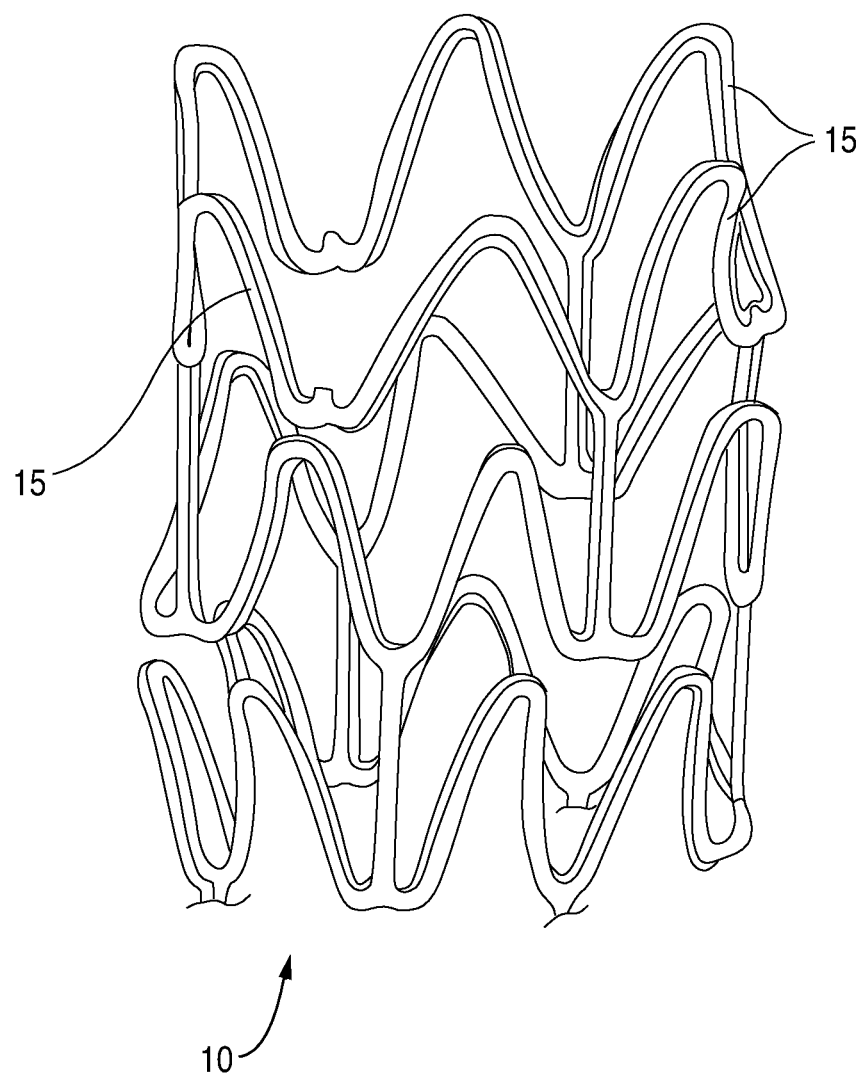
FIG. 1 depicts a stent.

Use of the singular herein includes the plural and vice versa unless expressly stated to be otherwise. That is, "a" and "the" refer to one or more of whatever the word modifies. For example, "an antioxidant" includes one antioxidant, two antioxidants, etc. Likewise, "a polymer" may refer to one, two or more polymers, and "the polymer" may mean one polymer or a plurality of polymers. By the same token, words such as, without limitation, "antioxidants" and "polymers" would refer to one antioxidant or polymer as well as to a plurality of antioxidants or polymers unless, again, it is expressly stated or obvious from the context that such is not intended.

As used herein, any ranges presented are inclusive of the end-points. For example, "a temperature between 10° C. and 30° C." or "a temperature from 10° C. to 30° C." includes 10° C. and 30° C., as well as any temperature in between.

As used herein, unless specifically defined otherwise, any words of approximation such as without limitation, "about," "essentially," "substantially" and the like mean that the element so modified need not be exactly what is described but can vary from the description by as much as ±15% without exceeding the scope of this invention.

As used herein, the use of "preferred," "preferably," or "more preferred," and the like to modify an aspect of the invention refers to preferences as they existed at the time of filing of the patent application.

The various embodiments of the present invention include methods to provide antioxidants to an implantable medical device that includes a polymer, and methods of packaging such devices. The polymer may be a biostable polymer, a biodegradable polymer, or a combination thereof. The antioxidants are provided to reduce degradation of the polymer during processing, and particularly, during sterilization, or to extend the shelf-life.

This invention relates to medical devices, and particularly implantable medical devices. Implantable medical devices include appliances that are totally or partly introduced, surgically or medically, into a patient's body or by medical intervention into a natural orifice, and which are intended to remain there after the procedure. More particularly, this invention is directed stents, a type of implantable medical device. Although the discussion that follows focuses on a stent as an example of a medical device, the embodiments described herein are easily applicable to other medical devices, and specifically, other implantable medical devices. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, closure devices for patent foramen ovale, vascular closure devices, cerebrospinal fluid shunts, and intrauterine devices.

Stents are generally cylindrically shaped devices that function to hold open, and sometimes expand, a segment of a blood vessel or other anatomical lumen such as urinary tracts and bile ducts. A "lumen" refers to a cavity of a tubular organ such as a blood vessel. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success. In addition to treatment for coronary artery disease such as atherosclerosis and restenosis, stents may be used for the maintenance of the patency of a vessel in a patient's body when the vessel is narrowed or closed due to diseases or disorders including, without limitation, tumors (m, for example, bile ducts, the esophagus, the trachea/bronchi, etc.), benign pancreatic disease carotid artery disease, peripheral arterial disease (PAD), and vulnerable plaque. For treatment of PAD, stents may be used in peripheral arteries such as the superficial femoral artery (SFA). For use of stents in the SFA appears to be more problematic than in coronary vessels and in other peripheral vascular beds, such as the iliac and carotid arteries.

Stents are typically composed of scaffolding that physically holds open and, if desired, expands the wall of a passageway. A stent may include a pattern or network of interconnecting structural elements or struts. FIG. 1 depicts an example of a three-dimensional view of a stent 10. The stent may have a stent pattern that includes a number of interconnecting elements or struts 15. The scaffolding can be formed from wires, tubes, or sheets of material rolled into a cylindrical shape. With respect to a stent, the scaffolding is the device body. In general, the body of a medical device may be the device in a functional form, but prior to the application of a coating or other material different from that of which the device body is formed.

Typically, stents are capable of being compressed, or crimped, onto a catheter so that they can be delivered to, and deployed at, a treatment site. Delivery includes inserting the stent through small lumens using a catheter and transporting it to the treatment site. Deployment includes expanding the stent to a larger diameter once it is at the desired location.

The stent must be able to satisfy several mechanical requirements. First, the stent must be capable of withstanding the structural loads, namely radial compressive forces, imposed on the stent as it supports the walls of a vessel lumen. This requires a sufficient degree of strength and rigidity or stiffness. In addition to having adequate radial strength, the stent should be longitudinally flexible to allow it to be maneuvered through a tortuous path and to enable it to conform to a deployment site that may not be linear or may be subject to flexure. The material from which the stent is constructed must allow the stent to undergo expansion which typically requires substantial deformation of portions of the stent. Once expanded, the stent must maintain its size and shape throughout its service life despite the various forces that may come to bear thereon, such as the cyclic loading induced by the beating heart. Therefore, a stent must be capable of exhibiting relatively high toughness which corresponds to high strength and rigidity, as well as flexibility. For stents used in the SFA, the mechanical requirements are high as the SFA is subjected to various forces, such as compression, torsion, flexion, extension, and contraction, which place a high demand on the mechanical performance of implants.

Although stents may be manufactured from materials such as metals and metal alloys (see paragraph [0031] of U.S. Patent Application Publication No. 2007/0020380 A1), stents may also be fabricated from polymers. As noted above, it may be desirable for implantable medical devices, such as stents, to be biodegradable. In many treatment applications, the presence of a stent in a body may be necessary for a limited period of time until its intended function of, for example, maintaining vascular patency and/or drug delivery is accomplished. Therefore, the device body, such as the scaffolding of a stent, may be fabricated from biodegradable, bioabsorbable, and/or bioerodable polymers can be configured to partially or completely erode away after the clinical need for them has ended.

Stents, whether manufactured from a polymer, from a metal, and/or from another material, may be coated. Coatings typically include one or more polymers, and may optionally include one or more drugs. A coating layer refers to material described as a layer or film "disposed over" or "formed on" a surface, and refers to such material that is deposited directly (to the substrate) or indirectly (applied to a previously applied material) over at least a portion of the surface. The terms "layer" and "coating layer" will be used interchangeably and refer to a layer, film, or coating layer as described in this paragraph. A coating layer may be applied by multiple applications or passes of a coating solution or of coating material. A coating may include one or more layers. An exemplary substrate is the outer surface of a stent, which is any surface, however spatially oriented, that is in contact with bodily tissue or fluids.

In addition to use in a coating or the device body, polymers may also form another portion of a device, or be used to fill indentations or pores in a device.

Fabricating polymer stents can involve processing steps that expose the polymer to high temperatures and other conditions such as radiation that can result in chemical degradation. The decrease in molecular weight can adversely affect mechanical properties and other properties of the polymer such as biodegradation behavior, and drug release properties.

Some of the process operations involved in fabricating a polymeric stent may include:

(1) forming a polymeric tube using extrusion;
(2) radially deforming the formed tube by application of heat and/or pressure;
(3) forming a stent from the deformed tube by cutting a stent pattern in the deformed tube;
(4) coating the stent with a coating including an active agent;
(5) crimping the stent on a support element, such as a balloon on a delivery catheter;
(6) packaging the crimped stent/catheter assembly; and
(7) sterilizing the stent assembly.

The manufacturing process of a stent exposes the stent to conditions such as heat, light, radiation, moisture, or other factors that can chemically degrade the stent polymer. As a non-limiting example, the decomposition of poly(L-lactide) (PLLA) may occur by free radical oxidation. Once free radicals are formed by oxidation and/or exposure to radiation or the like, the free radicals attack the polymer chain which results in a series of byproducts such as lactide monomers, cyclic oligomers and shorter polymer chains. In addition, decomposition may be catalyzed by the presence of oxygen, water, or residual metal such as from a catalyst. More specifically the polyester poly(L-lactide) is subject to thermal degradation at elevated temperatures, with significant degradation (measured as weight loss) occurring at about 150° C. and higher temperatures. The polymer is subject to random chain scission, and the degradation products also include aldehydes, and other cyclic oligomers. It is believed that a free radical chain process may be involved in the degradation.

Polymer molecular weight may significantly decrease during the processing operations used in the manufacture of a stent. A non-limiting example is the use of a PLLA polymer to manufacture a stent. An exemplary process including steps 1-7 results in a decrease of the weight average molecular weight from about 550 kg/mol to about 190 kg/mol. The decrease in polymer molecular weight results from extrusion (380 Kg/mol from the initial 550 kg/mol), radial expansion and laser cutting (280 kg/mol), and electron beam (25 KGy) sterilization (190 Kg/mol). Decrease of polymer molecular weight impacts the mechanical properties, such as radial strength of the polymeric stent, as well as potentially the drug release properties.

The decrease in the molecular weight of the polymer may have a profound impact on a biodegradable polymer stent. For biodegradable polymeric stents the scaffolding, which is formed from a polymer, supports the vessel for a time period. As the polymer biodegrades, there is a point in time at which the stent no longer supports the vessel. It is important for the stent to support the vessel for a time period long enough to prevent negative remodeling of the vessel after angioplasty and excessive recoil. For a biodegradable polymer stent, the vessel support is provided by the radial strength of the stent. The radial strength is largely impacted by the molecular weight of the polymer. As a result, a decrease in the polymer molecular weight may lead to a premature loss of radial strength and premature loss of vessel support. In addition to the premature failure of the stent, the decrease in polymer molecular weight may potentially result in fracture. If the molecular weight is lower, the biodegradable stent will biodegrade more quickly with a resultant loss in mass that is quicker. Premature mass loss may inhibit the formation of an endothelial layer over the stent. It is the formation of the endothelial layer that prevents thrombosis and inflammation from acidic by products resulting from polymer biodegradation.

As noted above, sterilization processes in particular may degrade polymers. Ethylene oxide sterilization, or irradiation, either gamma irradiation or electron beam (e-beam) irradiation, are typically used for terminal sterilization of medical devices. For ethylene oxide sterilization, the medical device is exposed to liquid or gaseous ethylene oxide that sterilizes through an alkalization reaction that prevents organisms from reproducing. Ethylene oxide penetrates the device, and then the device is aerated to assure very low residual levels of ethylene oxide because it is highly toxic. Ethylene oxide sterilization is often performed at elevated temperatures and with moisture to both speed up the processes of diffusion into and out of the device and enhance sterilization effectiveness. Polymer degradation can occur from the combination of heat and moisture. The mechanical properties of the stent may be changed due to prolonged exposure to elevated temperature and/or moisture.

Alternatively, irradiation may be used for terminal sterilization. It is known that radiation can alter the properties of the polymers being treated by the radiation. High-energy radiation tends to produce ionization and excitation in polymer molecules. Resultant physical changes can include embrittlement, discoloration, odor generation, stiffening, and softening, among others. In particular, the deterioration of the performance of polymers due to e-beam sterilization has been associated with free radical formation during radiation exposure and by reaction of these free radicals with other parts of the polymer chains. The reaction is dependent on e-beam dose, temperature, and atmosphere present, especially oxygen. Additionally, exposure to radiation, such as e-beam, can cause a rise in temperature of an irradiated polymer sample.

To prevent or reduce polymer degradation, antioxidants may be used. Generally, a molecule that protects from free radicals is an antioxidant, and more particularly, free radical scavengers are antioxidants. "Free radicals" refer to atomic or molecular species with unpaired electrons on an otherwise open shell configuration, and can be formed by oxidation reactions. These unpaired electrons are usually highly reactive, so radicals are likely to take part in chemical reactions, including chain reactions. Free radical scavengers operate through donation of an electron or hydrogen to a free radical, thus removing the free radical from further reaction. The free radical scavenger effectively competes with the polymer for the free radicals, and thus removes the free radicals from the reaction cycle.

Antioxidants may be added to the polymer to prevent, inhibit, or reduce polymer degradation, and the associated reduction in molecular weight. Antioxidants may be included in the package of an implantable medical device to prevent, inhibit, or reduce polymer degradation. The present invention is directed to methods of incorporating an antioxidant into an implantable medical device that includes a polymer, and methods of packaging an implantable medical device. The embodiments discussed below are applicable to a polymeric device, a device including a polymeric coating, or any device including a polymer.

Antioxidants are particularly important or crucial for biodegradable polymer stents for which the vessel wall support is provided by the polymer. Embodiments are particularly useful for a biodegradable polymeric stent manufactured from or including a biodegradable polyester, and especially poly(L-lactide) (PLLA), poly(L-lactide-co-glycolide) (PLGA), or combinations thereof. Embodiments are particularly useful for devices, whether biodegradable polymers, or made from other materials, that are coated with a coating including a biodegradable polyester, and especially poly(D,L-lactide) (PDLA).

Some embodiments of the present invention include methods of incorporating an antioxidant into an implantable medical device with a polymeric portion by exposing the device to a fluid including the antioxidant. As used herein, the word "incorporate" will be defined as the Merriam-Webster on-line dictionary defines it that is "to unite or work into something already existent so as to form an indistinguishable whole." The antioxidant is incorporated within, on the surface, or both, of a polymeric portion of the device. The polymeric portion, for example, may be a coating and/or a scaffolding. The resulting distribution of the antioxidant is not necessarily uniform throughout or on the exterior of the device.

Preferred antioxidants of the present invention are volatile antioxidants, which are those antioxidants with a vapor pressure of at least 1 mTorr, or alternatively, those antioxidants having a sufficient vapor pressure or that sublimate or vaporize sufficiently such that a concentration of 1 ppm, preferably at least 5 ppm, and more preferably, at least 10 ppm, may be obtained where the vapor pressure or concentration is determined at the temperature at which the device is exposed to the antioxidant. Volatile antioxidants are preferred as these antioxidants may be incorporated into a device as a result of exposure of the device to a vapor or gas including, but not limited to, the antioxidant. Although examples of antioxidants that are solid at room temperature may be used, the scope of the present invention is not so limited. Antioxidants that exist in the liquid or gas phase at room temperature and one atmosphere may also be used. If the sublimation or vaporization of the antioxidant is too low, too little antioxidant may be incorporated into a polymeric portion of the device. If the sublimation is too high, the antioxidant incorporated onto or within the device may be lost from the device prematurely. The determination of too low or too high depends upon the particular polymer used, and subsequent processing and storage conditions of the device after the incorporation of the antioxidant.

Presently preferred antioxidants are butylated hydroxytoluene (BHT) and butylated hydroxyanisole (BHA). The toxicological concerns with BHA and BHT are minimal as BHA and BHT are commonly used in the food industry. BHA is a relatively volatile solid with a melting temperature of 45 to 63° C. BHT can be sublimated at temperatures under its melting point (70° C.). Other antioxidants may also be used in the methods of the present invention.

The fluid including the antioxidant may be a gas, vapor, supercritical fluid, a liquid, or any combination thereof. The methods of the present invention differ from adding the antioxidant to a formulation or materials that are used in manufacturing the device. In other words, disposing a coating over a device wherein the coating includes an antioxidant differs because the antioxidant is added to the device at the same time that part of the device is formed or manufactured. Therefore, in some embodiments, the fluid is free of or substantially free of polymer, drug, and/or other materials (as used herein substantially free is about 10 ppm or less).

As used herein, exposure of the device to a gas including an antioxidant encompasses exposure to a gas, a vapor, a supercritical fluid, or any combination thereof, that includes an antioxidant.

Exposure may occur by placing the device in a chamber or other enclosed container filled with the gas, or the device may be placed in a chamber with a continuous flow or semi-continuous flow of gas through the chamber. For those embodiments using an enclosed chamber, the gas may be stagnant, or substantially stagnant, or alternatively a fan or other apparatus may be used to assure that there is some gas flow or convection.

Exposure may occur as a result of placing the device in an environment with a solid that sublimates or a liquid that evaporates. In some embodiments, the device is placed in a chamber or container along with the antioxidant, and then subsequently the entire chamber is heated, for example to 50° C., 60° C., or 70° C., resulting in sublimation or vaporization of the antioxidant. The antioxidant concentration in the environment increases and as a result, the antioxidant is incorporated into the polymeric portion of the device. The antioxidant that is placed into the chamber or container may be in a permeable container or package, in an open dish, or may be provided in any other manner that allows for sublimation or evaporation of the antioxidant. The device is exposed for a sufficient time and at sufficient concentration that the antioxidant is incorporated onto the device.

The concentration of antioxidant in the gas may be high enough to that there is a thermodynamic driving force resulting in diffusion of the antioxidant into the polymeric portion of the device and/or adsorption onto the surface of the device. The gas typically has at least 0.1 ppm of antioxidant and no more than 20% by volume antioxidant. Embodiments encompass the use of a gas having an antioxidant concentration of at least 1 ppm, at least 5 ppm, or at least 10 ppm, where the ppm is on a mass basis. Other embodiments encompass the use of a gas having an antioxidant concentration of at least 20 ppm, at least 50 ppm, at least 100 ppm, or at least 500 ppm. The concentration of antioxidant may be determined on a volume basis, and may be not more than 20% by volume as an upper limit, preferably not more than 15%, and more preferably not more than 10%. Embodiments of the invention encompass lower limits of not less than 0.005%, not less than 0.01%, not less than 0.05%, not less than 0.1%, not less than 0.5%, not less than 1.0%, and not less than 2.0% by volume of antioxidant in the gas used. In some embodiments, the antioxidant is not less than 0.001 µg/cm$^3$, preferably not less than 0.1 µg/cm$^3$, and more preferably, not less than 1 µg/cm$^3$.

The gaseous antioxidant can be absorbed on the surface of the device through polar-polar interaction to protect the device from oxidation. It can also acts as a scavenger of the residual oxygen in the package or container, and block the penetration of small oxygen molecules into the device. The antioxidant level may need to be higher if the device already includes the same antioxidant that is included in the gas to assure that there is a chemical potential gradient favoring diffusion into the polymeric portion of the device and/or adsorption onto the surface, rather than out of the device or desorption.

Because antioxidants are free radical scavengers, exposure of the antioxidant to an environment with free radicals may result in a premature reaction during the incorporation process, thus reducing the efficiency of the antioxidant incorporated. Therefore, in some embodiments, the gas may be free of, or substantially free of, oxygen which may be a factor in free radical formation. As used herein, substantially free of oxygen refers to not more than 0.01% by volume oxygen. However, a gas completely free of oxygen may not be possible.

Likewise, the medical device as manufactured in the atmospheric environment contains surface absorbed oxygen. Therefore, in some embodiments, some oxygen such as up to about 2% by volume may be present. The other protective gas present with oxygen and antioxidant may be nitrogen, helium, argon, or other gases or fluids that do not assist oxidation.

In other embodiments, the exposure is to a liquid including the antioxidant. The liquid chosen should not dissolve the polymer of the polymeric portion of the device. If the device includes a drug, the liquid may or may not dissolve the drug. The antioxidant may be dissolved or dispersed in the liquid, although in preferred embodiments, the antioxidant is dissolved in the liquid. The liquid may be an organic liquid, one the chemical composition of which includes carbon atom(s). In one embodiment, the liquid may not swell the polymer at all. For PLLA, non-limiting examples of such liquids are hexane, pentane, cyclohexane, and any combination of these. In another embodiment, the liquids are those that swell but do not dissolve the polymer. Liquids for use with PLLA include isopropyl alcohol, acetone, acetonitrile, tetrahydrofuran and combinations of these with a solvent in which the PLLA is soluble, such as without limitation, chloroform and hexafluoroisopropanol (HFIP). Other representative examples of liquids that may be used include, but are not limited to isopropanol, methanol, acetone, 1,4-dioxane, tetrahydrofuran (THF), dichloromethane acetonitrile, dimethyl sulfoxide (DMSO), and dimethylformamide (DMF), cyclohexane, toluene, xylene, ethyl acetate or combination of these non-solvents with a solvent in which the PLLA is soluble, such as, without limitation, chloroform, and hexafluoroisopropanol. Similarly, if the antioxidant is itself a liquid, it may be applied to the device without being either dissolved or dispersed in a liquid or vaporized, provided that the antioxidant does not dissolve or excessively swell the polymeric portion of the device.

In choosing a liquid, the solubility parameter may be used. The solubility parameter is provided in units of (cal/cm$^3$)$^{1/2}$. Solubility parameters of selected fluids are shown in Table 1.

TABLE 1

Solubility parameters of fluids at 25° C.

| Liquid | Solubility Parameter (cal/cm$^3$)$^{1/2}$ |
|---|---|
| Chloroform | 9.3 |
| Acetone | 10.0 |
| Chlorobenzene | 9.5 |
| Ethyl acetate | 9.1 |
| Ethylene dichloride | 9.8 |
| 2-ethyhexanol | 9.5 |
| 1,4-dioxane | 9.9 |

If the solubility parameter of the liquid is equal to that of the polymer, the polymer will likely swell or dissolve in the liquid. Dissolution is also a function of the polymer molecular weight. As the difference between the solubility parameters of the liquid and the polymer increases, the tendency of the polymer to swell in the liquid decreases.

The level of antioxidant in the liquid is not critical, but needs to be sufficient to at least partially cover the device. If a solvent that swells the polymer is chosen to dissolve the antioxidant, the antioxidant may diffuse into the polymeric portion of the device during the application of antioxidant. The coverage of the antioxidant on the device surface should be more than 1% of the surface area. The antioxidant deposition layer should be thin (<1 µm). In the subsequent drug-coating solution applications for forming a coating on at least a portion of the outer surface of the device, the sandwiched antioxidant can diffuse into the polymer layers in both directions, that is into the polymer of the device body and into the polymer of the coating.

The device may be exposed to the liquid by immersing the device, partially or completely, in the liquid, spraying the liquid onto the device, brushing or wiping the liquid on the device, or any combination thereof. The device may be immersed by dipping the device in a container of the liquid, or placing the device in a flow through apparatus. The liquid may be agitated in some manner, or may be stagnant, or substantially stagnant. If the liquid is sprayed onto the device the liquid may be allowed to evaporate, it may be wiped off, or liquid removal may use a flow of a gas, particularly a gas at a temperature above room temperature, over the surface of the device.

The exposure may occur at supercritical pressures if a supercritical fluid is used. The exposure to a gas, not including a supercritical fluid, or a liquid may occur at or about normal atmospheric pressure (760 mm Hg), or at pressures below normal atmospheric pressure.

The exposure of the device to the fluid may occur at room temperature, that is about 20° C. to about 25° C., or at an elevated temperature such as a temperature of at least 30° C., at least 40° C., or at least 50° C. It is believed that exposure to an elevated temperature will increase the rate of diffusion of the antioxidant into the polymeric portion of the device. When exposure is to a gas, elevated temperatures are preferable as the increased temperature is expected to increase the diffusion of the antioxidant into the polymeric portion of the device.

The exposure to the fluid may range from 1 second to 12 hours or more in duration. In some embodiments, the exposure may be from about 1 second to about 1 hour, about 30 seconds to about 5 minutes, from about 1 minute to about 15 minutes, from about 10 minutes to about an hour, or about 45 minutes to about 3 hours or more.

The exposure may be intermittent. In particular, if the antioxidant is included in a liquid that is sprayed onto the device, the liquid may be sprayed onto the device at room temperature or slightly higher such as 30° C. to 35° C., and then exposed to flow of gas to remove the liquid which is at a higher temperature, such as about 40° C. to about 50° C., or even higher. Evaporation of the liquid may leave some solid antioxidant at the surface of the device. Although some of the antioxidant may sublime, the increased temperature may enhance diffusion of the solid antioxidant into the device.

A liquid may be chosen that plasticizes the polymer. It is also believed that if the liquid plasticizes the polymer and decreases the glass transition temperature of the polymer, diffusion of the antioxidant into the polymer may be enhanced. In general, diffusion of a substance through a polymer is significantly higher above the glass transition temperature where the polymer chains may move more freely as compared to below the glass transition temperature. However, even below the glass transition temperature, and particularly within about 10° C. or about 5° C. of the glass transition temperature, the diffusion coefficient of a substance should be higher as compared to temperatures that are much lower, such as 20° C. below the glass transition temperature. Without being bound by theory, it is believed that exposing the polymeric portion of the device to a liquid which is also a plasticizer for the polymer may not only increase diffusion of antioxidant into the polymeric portion of the device, but also may help reduce loss of the antioxidant once it has diffused into the device. If the liquid chosen is one for which the diffusion is higher than of the antioxidant, the antioxidant may be effectively "frozen" into the polymer. As the liquid diffuses out, the plasticizing effect is lost with the result that the glass transition temperature is increased. The increase in the glass transition temperature results in a lower diffusion coefficient for the antioxidant, and thus the antioxidant may be "frozen" into the polymer.

For exposure to a gas, or a liquid, the device may be placed in contact with the gas or liquid including the antioxidant, and then the temperature of the environment and/or the device is subsequently raised. In some embodiments, the temperature of the gas, liquid, and/or device is raised prior to the exposure.

The antioxidant may be incorporated into the device nonuniformly. The antioxidant concentration may be higher at or near the surface if the time frame of exposure is not sufficient to allow the antioxidant to diffuse throughout the entire polymeric portion of the device. Thus, in some embodiments, the concentration of the antioxidant decreases as the distance from the surface increases. In some embodiments, the antioxidant incorporated into the device is not present throughout the entire polymeric portion of the device, such as throughout the thickness of the scaffolding, or the entire thickness of the coating. In other embodiments, the antioxidant is incorporated on and/or near the surface, such as without limitation, the first 5000 Å from the surface. If the polymeric portion of the device is a coating, the antioxidant may be incorporated throughout the coating at essentially a uniform level. It is believed that incorporation of the antioxidant in this manner, which is with more near and/or at the surface, will reduce degradation as oxygen is a major factor in degradation, and oxygen must diffuse into the polymeric portion of the device.

In some embodiments, the exposure results in a level of at least 1 µg antioxidant/g of polymer, at least 5 µg antioxidant/g of polymer, or at least 10 µg antioxidant/g of polymer. In other embodiments, the exposure results in incorporation of at least 1 µg antioxidant/g of coating, at least 5 µg antioxidant/g of coating, or at least 10 µg antioxidant/g of coating. The level of antioxidant provided may be sufficient to prevent degradation of the polymer. If the level is too high, the antioxidant may impact the mechanical properties of the polymer and or drug release. Also, the level should be within the range that is toxicologically acceptable, or within the levels set by regulatory authorities.

A non-limiting example of exposure to a fluid including an antioxidant is placing a device in a chamber, removing the air from the chamber, and filling the chamber with a gas including an antioxidant. Alternatively, as mentioned above, an antioxidant such as, without limitation, solid BHT or BHA, may be placed in the chamber in an open dish or permeable container, the device placed in the chamber, air or other gasses removed to form a vacuum and allowing the antioxidant to sublime or evaporate. The temperature in the chamber may be raised after the device has been placed inside the chamber, or prior to placing the device and/or antioxidant into the chamber.

As used herein, the exposure to a fluid encompassing an antioxidant refers to an exposure of the device by placing the device in contact with a fluid including an antioxidant that is more than an incidental exposure. An incidental exposure is unlikely to result in incorporation of the antioxidant into the device, and particularly unlikely to incorporate antioxidant at a sufficient level to inhibit or limit degradation of the polymer.

The methods of the present invention may be integrated into a manufacturing process for a polymeric stent. The exposure may occur at any point, or multiple points, in the manufacture. In some embodiments, the manufacturing scheme involves more than one exposure to a fluid including an antioxidant, and each exposure may be to the same, or to a different fluid, and to the same or to a different antioxidant than previously used. In some cases, the exposure may be used to replace antioxidant lost in processing as a result of sublimation or other processes.

In some embodiments, a polymer tube formed by extrusion may be exposed to a fluid prior to radial and/or axial expansion and cutting a stent pattern into the tube such as with a laser to form a polymeric stent. The exposure may replace antioxidant lost during the extrusion process and reduce degradation during the subsequent processes. In another embodiment, the exposure may be after cutting, but prior to coating. This exposure may occur in addition to the exposure prior to radial expansion and laser cutting. The advantage of the exposure prior to coating, and particularly after cutting a stent pattern and prior to coating is to assure that antioxidant is incorporated into the polymeric scaffolding to limit the degradation of the polymer due to sterilization. The subsequent formation of a coating on the device may increase the time and difficulty of incorporating antioxidant into the scaffolding of the device. The device may be additionally exposed to a fluid to incorporate an antioxidant after the coating has been applied.

In some manufacturing schema, after cutting, the stent is washed with an organic fluid that does not dissolve the polymer. For example, a PLLA stent can be rinsed or washed with isopropanol. Thus, in some embodiments, the two processing operations may be combined by adding antioxidant to the isopropanol used in the washing or rinsing operation. Exposure at these points in the manufacturing process results in incorporation of the antioxidant into the polymeric scaffolding, or the device body.

The exposure may occur after forming a coating on the polymeric stent, and result in incorporation of the antioxidant into the coating. In some embodiments, antioxidant may also be incorporated into the polymeric device body in addition to the coating. The antioxidant may also incidentally migrate from the coating into the polymeric device body. The fluid may be the same as or different from the fluid used in the coating operation.

As noted above, for the non-limiting example of a PLLA biodegradable stent, the molecular weight decreased from 400 to about 300 kg/mol during radial expansion and laser cutting with a further decrease to 200 kg/mol after sterilization. Exposure prior to radial expansion and laser cutting, and optionally before and/or after a coating is formed on the device, may reduce the decrease in molecular weight in both the device body and the coating that is due to subsequent processing. In particular, polymer degradation resulting from sterilization may be reduced. Alternatively and/or additionally, sterilization may be performed at room temperature, about 20° C. to about 25° C., rather than temperatures below room temperature because the antioxidant reduces or inhibits polymer degradation. As the molecular weight is critical to the radial strength of the biodegradable stent, any reduction in molecular weight decrease is likely to improve the stent performance. The molecular weight of a polymer in the coating impacts both drug release and biodegradation rates, and therefore, a reduction in the decrease of the molecular weight of the polymer in the coating also improves stent performance.

The polymeric portion of the device that is exposed may already include an antioxidant. As a non-limiting example, the polymer used to extrude the tube from which the stent is manufactured may have antioxidant added during, or prior to, the extrusion process. Another example, without limitation, is inclusion of an antioxidant in a coating formulation that is disposed over at least a portion of the device's outer surface to form a coating on the device. The antioxidant in the fluid may be the same as or different from the one already included in the polymeric portion of the device.

Antioxidants may be added directly to the polymer forming the body of the stent, to the coating formulation, and/or to other polymer used to form a portion of the device. However, addition of the antioxidant by exposure to a fluid avoids potential changes that may occur as a result of adding the antioxidant to a formulation. Non-limiting potential changes include any impact that the antioxidant may have on polymer crystallization or the distribution of the drug in the coating. The presence of the antioxidant may limit the temperatures that may be used in a process, or may limit the humidity conditions under which a process may occur. The distribution of solid antioxidant that is added to solid polymer resin prior to or during extrusion may be non-uniform. Further, adsorption at the surface of the device through polar-polar interaction of antioxidants such as BHT may protect the device from oxidation.

Although one alternative to the methods of the present invention is using higher molecular weight polymers as starting materials, processing with the higher molecular weight materials is more difficult, and in some cases, not possible.

In some embodiments, exposure of the device to a fluid including an antioxidant results in the polymer of the device, as measured at the end of the manufacturing process, having a weight average molecular weight that is at least 2%, at least 5%, at least 10%, at least 15%, or at least 20% greater than that of a polymer of a device body that has not been exposed to such a fluid. In some embodiments, the result of the exposure is the polymer of the device body has a weight average molecular weight that is at least 5%, at least 10%, or at least 15% greater after one or more processing operations such as radial expansion, stent pattern cutting, or coating. Incorporation of antioxidant by exposure to a fluid reduces the molecular weight decrease occurring due to sterilization. In some embodiments, at least 5%, at least 10%, at least 20% reduction in molecular weight decrease resulting from sterilization is obtained, as measured by comparing the weight average molecular weight before and after sterilization.

Some medical devices also includes drug, either in the body of the device, distributed in a coating on the device, or in another polymer forming a portion of the device. Degradation of the polymer may therefore impact drug release rate. In some embodiments, the exposure of a device including a drug to a fluid including an antioxidant assures that the drug release profile is essentially unchanged by sterilization. In some embodiments, the release profiles before and after sterilization are similar as measured by the FDA similarity factor f2 (typically used for dissolution profiles).

In the methods described above, although the antioxidant is added to reduce or inhibit polymer degradation, it may also reduce or inhibit degradation of other components of the device, such as a drug, that are subject to degradation by oxidation.

Other aspects of the present invention are methods of packaging medical devices, particularly implantable medical devices, to extend the shelf-life of the packaged device, and kits of the devices so packaged. Methods of extending shelf-life of packaged medical device are described in paragraphs [0017]-[0020] of U.S. Patent Application Publication No. 2007/0020380 A1. Although these methods are discussed in terms of preventing drug degradation, these methods may also be used to extend the shelf-life by reducing the molecular weight degradation of polymers included in the device. The methods may also be used to prevent or inhibit polymer degradation during sterilization. The level of antioxidant required to prevent polymer degradation and to prevent drug degradation may differ, or may be the same, or may overlap. Based on the disclosure of U.S. Patent Application Publication No. 2007/0020380 A1 in conjunction with the disclosure herein, one of skill in the art would be able to determine the appropriate levels without undue experimentation.

The device may be placed into a package with a permeable or porous container including an antioxidant that sublimes to fill the package. The package may be a Tyvek pouch or the like. The device may be crimped onto a catheter to form an assembly. The device may be sterilized before or after placement in the package. With regard to the packaging methods herein, reference to a device also encompasses an assembly of a device on a catheter, or other delivery apparatus.

In other embodiments, the device may be packaged in a primary package that is permeable and then placed in a second impermeable, or substantially impermeable package, with the antioxidant in the secondary package. As used herein, a substantially impermeable package refers to one for which the antioxidant permeation rate is not more than 1 µg/min/m². As used herein, secondary package does not refer to boxes or other containers in which packaged medical devices are placed for shipment. Antioxidant may be present in the primary or secondary package as a solid, gas, or fluid form. Preferably pure solid or liquid antioxidant is not inserted directly "as is" into the primary package as it may stick or attach to the device. The primary and/or secondary package interior may be filled with a gas or fluid including the antioxidant. The interior of the primary or secondary package may include antioxidant as a result of placing antioxidant, whether in solid form or otherwise, into the secondary package, coating the interior surfaces of the primary and/or secondary package, and/or the exterior surface of the primary package with a material including the antioxidant. Antioxidant in the second package may diffuse through the primary package to increase the antioxidant level in the primary package. The interior of the primary package refers to the space inside the primary package, and the interior of the secondary package refers to the space within the secondary package, and when the primary package is placed inside the secondary package, the space between the primary and secondary package.

A carrier material including the antioxidant may be placed in the primary and/or secondary package. A non-limiting example of such a carrier is a permeable or porous container including the antioxidant. The carrier may be a porous bead, or a woven material or absorbent fiber that includes the antioxidant. The carrier may in the form of a tablet, powder, or granular material which includes the antioxidant and optionally inert materials. The carrier may be placed in a permeable container or pouch. A non-limiting example is a strip of a woven material with antioxidant adsorbed on the surface, or absorbed within the fibers. Preferably, the carrier has a high surface area to allow the antioxidant to sublime. A carrier that is a container may be a plastic permeable container, or another type of container such as a sealed permeable pouch.

In some embodiments, the antioxidant may be part of the packaging itself, or integrated with or into the packaging, as a result of absorption or diffusion into the walls or the film or other material forming the package. In other embodiments, the antioxidant is integrated with the package as a result of the inclusion of an inner liner or one or more laminates of a multi-laminate film having a high level of antioxidant that forms part of either the primary or the secondary package or both. The material forming the primary and/or secondary package may be integrated with an antioxidant because the material itself has a higher level of antioxidant. In such embodiments, the quantity of antioxidant present is greater than the amount that is added to polymer packaging films to inhibit or prevent degradation of the polymer of the packaging material. The antioxidant level is higher than the "as received" level typically present in such packaging material. The higher level may result from specifying a package with a higher level of antioxidant in the material forming the package, or the addition of or formation of a liner or layer including antioxidant at a higher level in the package. The higher level of antioxidant that is added or integrated with the package material is a sufficient quantity or level to allow for sublimation and/or evaporation of the antioxidant into the interior of the package. Likewise, as used herein with respect to the coating of the packaging, a "coating" is not a polymer or film of the packaging that incidentally includes antioxidant to prevent or inhibit degradation of the polymer of the packaging.

In those embodiments in which the antioxidant is included in a coating on the interior or exterior of the package, included in a liner or laminate of the package, or including in the material forming the package, the antioxidant may be present at a level of 2 µg/cm$^2$ to 10 mg mg/cm$^2$, preferably 10 µg/cm$^2$ to 5 mg/cm$^2$, and more preferably 50 µg/cm$^2$ to 10 mg/cm$^2$.

As noted in paragraph [0018] of U.S. Patent Application Publication No. 2007/0020380 A1, to increase the rate of sublimation, one may optionally heat the entire packaged device to a temperature from about 20° C. and, 70° C. for a short period of time (e.g., about 10 seconds, about 20 seconds, about 30 seconds, about 40 seconds, about 50 seconds, about 60 seconds, about 90 seconds, or about 120 seconds). Embodiments encompass temperatures between 20° C. and, 70° C., such as without limitation, from about 20° C. to about 30° C., from about 25° C. to about 40° C., from about 30° C. to about 50° C., and from about 40° C. about 60° C. The increased temperature for a short time period allows the antioxidant gas (e.g., BHT gas) to fill the space of the primary and/or secondary package. A preferred temperature for a biodegradable polymeric stent and/or coating is a temperature that is in the neighborhood of the glass transition temperature of the polymer (e.g. 55° C. for PLLA) but also high enough that sublimation of the solid occurs at a rate that at least 10% of antioxidant can be sublimated in 24 hrs.

A sufficient amount of antioxidant is added to obtain at least 0.001 ppm of antioxidant and no more than 99% by volume antioxidant in the interior of the primary and/or secondary package that is for the fluid of the interior of the primary and/or secondary package that surrounds the device and/or the primary package. Embodiments encompass antioxidant concentrations of at least 0.01 ppm, at least 0.1 ppm, at least 1 ppm, at least 5 ppm, or at least 10 ppm, where the ppm is on a mass basis in the interior of the primary and/or secondary package. Embodiments encompass antioxidant concentrations of at least 0.001 µg/cm$^3$, at least 0.01 µg/cm$^3$, at least 0.1 µg/cm$^3$, at least 1 µg/cm$^3$, at least 5 µg/cm$^3$, or at least 10 µg/cm$^3$ in the interior of the primary and/or secondary package. The concentration of antioxidant may be determined on a volume basis, and may be not more than 30% by volume as an upper limit, preferably not more than 25%, and more preferably not more than 20%. Embodiments of the invention encompass lower limits of not less than 0.0005%, not less than 0.001%, not less than 0.005%, not less than 0.01%, not less than 0.05%, not less than 0.1%, and not less than 0.5% by volume. The measurement of antioxidant concentration may be made after exposure to an elevated temperature, or about 30 minutes to about 24 hours after packaging.

The fluid (such as a gas) filling the packaging, particularly the primary package, is free of, or essentially free of, oxygen since oxygen is a known factor increasing the rate of degradation for many polymers and drugs. Preferably the fluid filling the primary and secondary packages is an inert gas, such as without limitation, argon, nitrogen, and/or helium.

The packaging methods of the present invention may be used for packaging a device either before or after sterilization. If packaged prior to sterilization, the polymer of the device so packaged may have a weight average molecular weight that is at least 5%, at least 10%, at least 15%, or at least 20% greater than the polymer sterilized after packaging without the addition of antioxidant. In some embodiments, the drug release profiles before and after sterilization for a device packaged with antioxidant are similar as measured by the FDA similarity factor f2.

By packaging the device with antioxidant in the package, it is believed that the antioxidant will react with oxygen that incidentally permeates or seeps into the package. It will also react with residual oxygen in the interior of the package, or absorb on the surface of the device. Thus, the packaging methods of the present invention extend the shelf-life of the packaged device. In some embodiments, the shelf-life is increased by at least 1 month, at least 2 months, at least 3 months, or at least 6 months. In some embodiments, the shelf-life is increased by at least 10%, at least 25%, or at least 50%. In some embodiments, the polymer of the device packaged according to the methods of the invention may have a higher weight average molecular weight at 3 months, at 6 months, at 12 months, or at 24 months, than the polymer of a device that is not so packaged.

In some embodiments, packaging a device including a polymer with an antioxidant in the packaging environment leads to some incorporation of the antioxidant in the device and/or a polymer of the device. If the device does not include this particular antioxidant, diffusion of antioxidant into a polymer of the device may occur over time. If the device includes the same antioxidant included in the package, diffusion will occur only if the chemical potential gradient is sufficient, or that is if the concentration of the antioxidant in the package is sufficient. Incorporation of an antioxidant in a device as described above may be accomplished by placing the device in a sealed container, such as a package, with antioxidant that sublimates into the gas phase in the container.

In other embodiments, packaging the device with antioxidant is to prevent potential degradation. The antioxidant present in the package may act as an oxygen scavenger, and thus reduce the potential degradation resulting from oxygen that does penetrate the package over time. Thus, in some embodiments, the level of antioxidant included for methods of packaging may be lower than those levels used for purposes of incorporating antioxidant into the device. In some embodiments, the packaging methods may be used both to protect the device from oxygen that seeps into the package, or is absorbed on the surface of the device as well as for incorporation of antioxidant into a polymeric portion of the device.

Some embodiments of the present invention include kits containing an implantable medical device, either as is or crimped onto a catheter or onto another apparatus for delivery, in any of the above packaging configurations. The fluid in the interior of the primary and/or secondary package of the kit may have antioxidant present at the levels described above.

Antioxidants and Free Radical Scavengers

As noted above antioxidants are a type of free radical scavengers. Some representative examples of free radical scavengers that may be used in the methods of the present invention include, without limitation, oligomeric or polymeric proanthocyanidins, polyphenols, polyphosphates, polyazomethine, high sulfate agar oligomers, chitooligosaccharides obtained by partial chitosan hydrolysis, polyfunctional oligomeric thioethers with sterically hindered phenols, hindered amines such as, without limitation, p-phenylene diamine, trimethyl dihydroquinolones, and alkylated diphenyl amines, substituted phenolic compounds with one or more bulky functional groups (hindered phenols) such as tertiary butyl, arylamines, phosphites, hydroxylamines, and benzofuranones. Also, aromatic amines such as p-phenylenediamine, diphenylamine, and N,N' disubstituted p-phenylene diamines may be utilized as free radical scavengers. Other examples include, without limitation, butylated hydroxytoluene ("BHT"), butylated hydroxyanisole ("BHA"), L-ascorbate (Vitamin C), Vitamin E, herbal rosemary, sage extracts, glutathione, melatonin, carotenes, resveratrol, ethoxyquin, rosmanol, isorsmanol, rosmaridiphenol, propyl gallate, gallic acid, caffeic acid, p-coumeric acid, p-hydroxy benzoic acid, astaxanthin, ferulic acid, dehydrozingerone, chlorogenic acid, ellagic acid, propyl paraben, sinapic acid, daidzin, glycitin, genistin, daidzein, glycitein, genistein, isoflavones, and tertbutylhydroquinone. Examples of some phosphites include di(stearyl)pentaerythritol diphosphite, tris(2,4-di-tert-butyl phenyl)phosphite, dilauryl thiodipropionate and bis(2,4-di-tert-butyl phenyl)pentaerythritol diphosphite. Some examples, without limitation, of hindered phenols include octadecyl-3,5,di-tert-butyl-4-hydroxy cinnamate, tetrakis-methylene-3-(3',5'-di-tert-butyl-4-hydroxyphenyl)propionate methane 2,5-di-tert-butylhydroquinone, ionol, pyrogallol, retinol, and octadecyl-3-(3,5-di-tert-butyl-4-hydroxyphenyl)propionate Polymers The embodiments of the various methods and kits described herein are applicable to medical devices including any polymer(s). However, preferred polymers for use with a device include, without limitation: biodegradable polymers, biodegradable polyanhydrides, poly(ether-esters), or polyesters such as poly(L-lactide), poly(D,L-lactide), poly(L-lactide-co-D,L-lactide), poly(L-lactide-co-glycolide), poly(D,L-lactide-co-glycolide), poly(L-lactide-co-caprolactone), poly(glycolide-co-caprolactone), poly(D,L-lactide-co-caprolactone), polyethylene glycol, polyethylene oxide, other polymers formed from one or more of L-lactide, D-lactide, meso-lactide, glycolide, and caprolactone, and combinations thereof, and blends of the aforementioned polymers. Preferred polymers for a biodegradable scaffolding include, without limitation, poly(L-lactide) (PLLA), and poly(L-lactide-co-glycolide) (PLGA) where the mol % lactide varies from 0 to 100%, such as, without limitation, PLGA with 85% lactide and 15% glycolide. When reference is made to a polymer having X mol % of a particular monomer such refers to the mole percent of the monomer used to form the polymer.

Representative examples of polymers that may be included in an implantable medical device, such as without limitation the device body and/or a coating, include, but are not limited to: poly(N-acetylglucosamine) (Chitin), Chitosan, polyesters, biodegradable polyesters, poly(hydroxyvalerate), poly(lactide-co-glycolide), poly(hydroxybutyrate), poly(hydroxybutyrate-co-valerate), polyorthoesters, polyanhydrides, poly(glycolic acid), poly(glycolide), poly(glycolide-co-trimethylene carbonate), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, and any blends and any copolymers thereof.

As used herein, the terms poly(D,L-lactide), poly(L-lactide), poly(D,L-lactide-co-glycolide), and poly(L-lactide-co-glycolide) are used interchangeably with the terms poly (D,L-lactic acid), poly(L-lactic acid), poly(D,L-lactic acid-co-glycolic acid), and poly(L-lactic acid-co-glycolic acid), respectively.

Active Agents

Active agents, or drugs, may optionally be included in the device. The active agent may be either in the body of the implantable medical device such as a stent, and/or in a coating on the device, or in another part of the device. These active agents can be any agent which is a therapeutic, prophylactic, or a diagnostic agent, or any agent that is used to treat a disease or condition. Preferred active agents include, without limitation: everolimus, sirolimus, biolimus, paclitaxel, or zotarolimus. Other active agents that may be included in the implantable medical devices are listed in paragraphs [0029] and [0030] U.S. Patent Application Publication No. 2007/0020380 A1.

Definitions

As used herein, "therapeutic agent," "drug," "active agent," "bioactive agent," or "pharmaceutically active agent," which will be used interchangeably, refers to any substance that, when administered in a therapeutically effective amount to a patient suffering from a disease or condition, has a therapeutic beneficial effect on the health and well-being of the patient. A therapeutic beneficial effect on the health and well-being of a patient includes, but is not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent," "drug," "active agent," "bioactive agent," or "pharmaceutically active agent," also refers to pharmaceutically acceptable, pharmacologically active derivatives of those drugs specifically mentioned herein, including, but not limited to, salts, esters, amides, prodrugs, active metabolites, analogs, and the like.

As used herein when an implantable medical device, such as a stent, is said to be fabricated from a polymer (polymeric stent or polymeric device), or the device or device body is composed of a polymer, or is referred to as a "polymeric stent" or "polymer stent," it means the body of the device is made from a polymer or a polymer formulation. Thus, for a "polymeric stent" the body of the stent may be completely, or substantially completely, a polymer, or made from a composition including a polymer and other materials such that the polymer is the continuous phase. The body of the stent may be at least 50% by weight polymer. In other embodiments, polymer may be at least 50% by volume of the composition forming the stent body. Similarly, a tube referred to as a polymeric tube or a polymer tube may be formed from a polymer or a polymer formulation, may be completely or substantially completely polymer, may have a continuous phase of polymer, or may have at least 50% by weight or at least 50% by volume polymer. Only one criterion needs to be satisfied.

As used herein, the terms "biologically degradable" (or "biodegradable"), "biologically erodable" (or "bioerodable"), "biologically absorbable" (or "bioabsorbable"), and "biologically resorbable" (or "bioresorbable"), are used interchangeably, and refer to polymers, coatings, and materials that are capable of being completely or substantially completely, degraded, dissolved, and/or eroded over time when exposed to physiological conditions, and can be gradually resorbed, absorbed and/or eliminated by the body, or that can be degraded into fragments that can pass through the kidney membrane of an animal (e.g., a human). Conversely, a "biostable" refers to a material that is not biodegradable.

As used herein, "degradation" of a polymer refers to at least a decrease in the molecular weight of the polymer, and also encompasses other undesirable changes such as cross-linking, discoloration and oxidation, and/or the appearance of other chemical species. Degradation of the polymer is the result of physical and chemical processes and is distinguished from biodegradation that occurs once implanted in the body. Thus, a biodegradable polymer may "degrade" during polymer processing, and "biodegrade" when the polymer is implanted in the body. The mechanisms of degradation in the body, "biodegradation" (hydrolysis etc.) may be different than the mechanisms of processing degradation.

EXAMPLES

The following example is provided to aid in understanding the invention, but it is to be understood that the invention is not limited to the particular materials or procedures of the example.

Example 1

Sublimation of BHT

Figure 2:
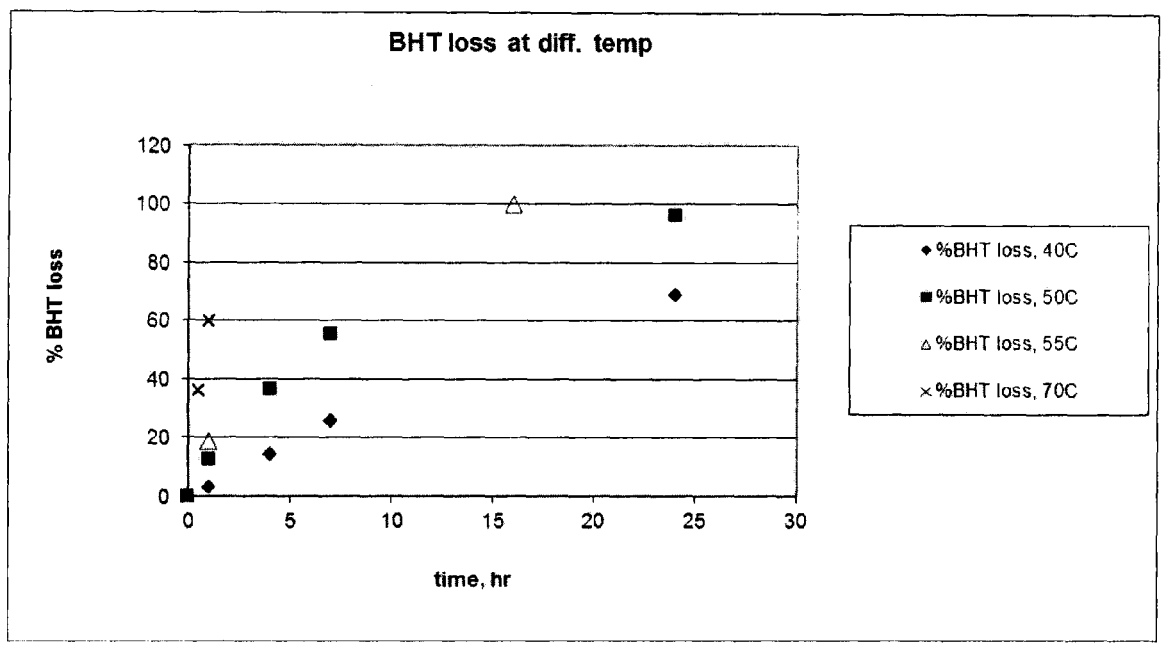
FIG. 2 depicts the mass loss of butylated hydroxytoluene (BHT) powder versus time for different temperatures.

A study was performed that demonstrated the sublimation of BHT. In the first experiment, 100 mg of BHT was weighed in an aluminum pan and heated in a convection oven at 55° C. At 1 hour and 16 hours after placement in the oven, the pan was removed and weighed. At the next time point, after leaving the pan in the oven overnight, no solids were present. A subsequent experiment was carried out utilizing a temperature of 70° C., and weighted at time-points of 30 minutes and 1 hr. The melting point of BHT is 70° C. so this temperature was the highest temperature in the experiments. Additional data was obtained from measurements at 40° C. and 50° C. with weight measurements at time-points of 1, 4, 7 and 24 hours. The results are illustrated in FIG. 2 which shows a plot of BHT weight loss vs. time for the different temperatures. As shown in FIG. 2, it is clear that BHT sublimation occurred at temperatures under 70° C.

Figure 3:
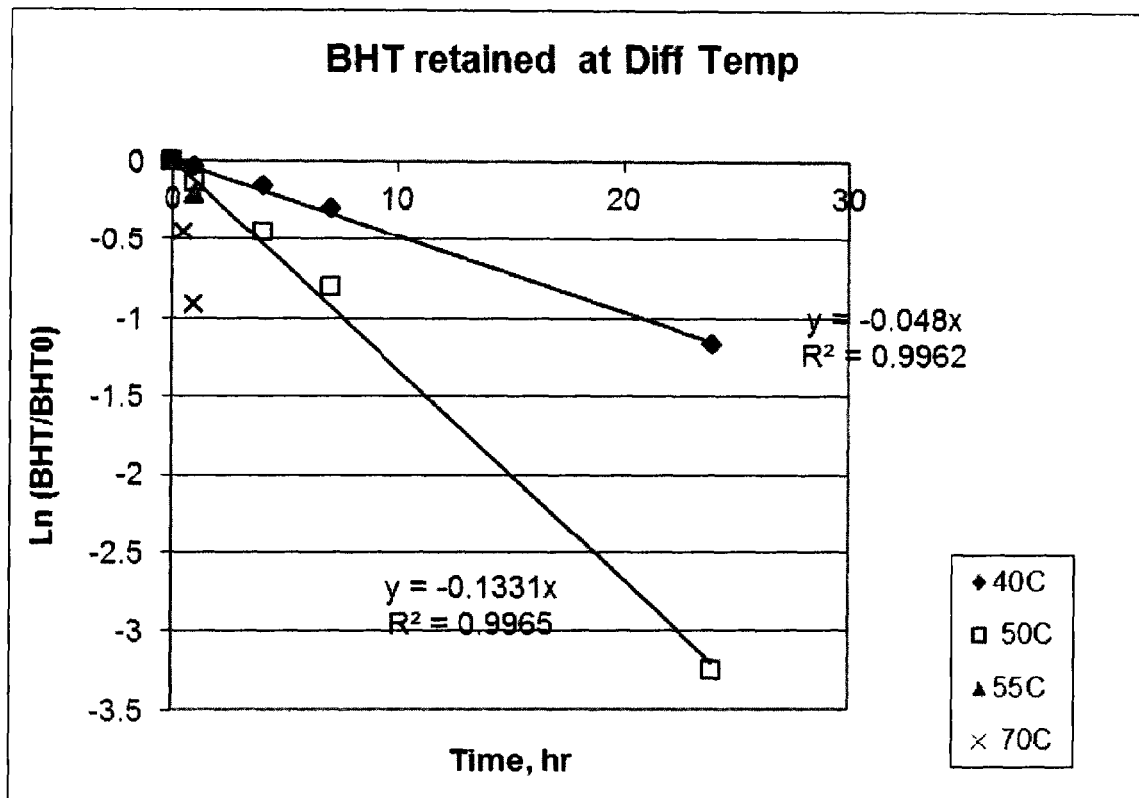
FIG. 3 is a plot of the ratio of BHT remaining to the initial mass of BHT versus time for different temperatures.

FIG. 3 is a plot of Ln (BHT/BHT$_0$) vs. time. A log-linear profile was observed at 40° C. and 50° C., indicating first order sublimation kinetics. No curve fitting was performed for the data at 55° C. and 70° C. because there were an insufficient number of data points. Equation 1 represents $1^{st}$ order kinetics, $$\text{Ln}\frac{BHT}{BHT_0} = -kt \qquad (1)$$

where BHT/BHT$_0$ is the ratio of BHT remained in the pan at time t and k is the sublimation rate constant at the experimental temperature. Using equation 1, the half-lives for BHT sublimation are ~13 hr at 40° C. and ~5 hr at 50° C.

Based on the curve fitting in FIG. 5, $k_{40C}$=0.048 and $k_{50C}$=0.1331. Using the Arrhenius equation shown in Equation 2, $$\text{Ln}\frac{k_2}{k_1} = \frac{E_a}{R}\left[\frac{T_2 - T_1}{T_1 T_2}\right] \qquad (2)$$

where R is the gas constant (1.987) and $E_a$ is the sublimation activation energy, the activation energy for BHT sublimation is 20.5 kcal/mol. The rate constant at other temperatures can be readily calculated from equations 1 and 2.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention.

What is claimed is:

1. A kit comprising:
an implantable medical device comprising a polymer and optionally comprising a device antioxidant;
a primary package with an interior, an interior surface and an exterior surface, the primary package comprising a second antioxidant, which may be the same as or different from the device antioxidant; and
a secondary package with an interior and an interior surface, the secondary package being impermeable or substantially impermeable to the second antioxidant;
wherein the implantable medical device is sealed inside the primary package, and a fluid filling the interior of the primary package comprises at least 0.001 μg/cm³ of the second antioxidant;
wherein the primary package is sealed within the secondary package; and
wherein the primary package is permeable to the second antioxidant.

2. The kit of claim 1, wherein a carrier comprising the second antioxidant is sealed within the primary package, the primary package interior surface is at least partially coated with a material comprising the second antioxidant, the second antioxidant is integrated with the primary package, or a combination thereof.

3. The kit of claim 1, wherein a carrier comprising the second antioxidant is sealed within the primary package, a carrier comprising the second antioxidant is sealed within the secondary package, the primary package exterior surface is at least partially coated with a material comprising the second antioxidant, the secondary package interior surface is at least partially coated with a material comprising the second antioxidant, the second antioxidant is integrated into the primary package, the second antioxidant is integrated into the secondary package, or any combination thereof.

4. The kit of claim 1, wherein the implantable medical device is a stent.

5. The kit of claim 4, wherein the stent is a bioabsorbable stent.

6. The kit of claim 3, wherein a carrier comprising the second antioxidant is sealed within the primary package, a carrier comprising the second antioxidant is sealed within the secondary package, or a combination thereof.

7. The kit of claim 3, wherein the primary package exterior surface is at least partially coated with a material comprising the second antioxidant, the secondary package interior surface is at least partially coated with a material comprising the second antioxidant, or a combination thereof.

8. The kit of claim 3, wherein the second antioxidant is integrated into the primary package, the second antioxidant is integrated into the secondary package, or a combination thereof.

9. The kit of claim 1, wherein the second antioxidant is solid and is placed inside the secondary package.

10. The kit of claim 1, wherein the fluid filling the primary package is an inert gas.

11. The kit of claim 10, wherein the inert gas is argon, nitrogen, helium, or a combination thereof.

12. The kit of claim 1, wherein the second antioxidant is butylated hydroxytoluene (BHT), butylated hydroxyanisole (BHA), or a combination thereof.

13. The kit of claim 3, wherein the second antioxidant is butylated hydroxytoluene (BHT), butylated hydroxyanisole (BHA), or a combination thereof.

14. The kit of claim 6, wherein the second antioxidant is butylated hydroxytoluene (BHT), butylated hydroxyanisole (BHA), or a combination thereof.

15. The kit of claim 7, wherein the second antioxidant is butylated hydroxytoluene (BHT), butylated hydroxyanisole (BHA), or a combination thereof.

16. The kit of claim 8, wherein the second antioxidant is butylated hydroxytoluene (BHT), butylated hydroxyanisole (BHA), or a combination thereof.

17. The kit of claim 9, wherein the second antioxidant is butylated hydroxytoluene (BHT), butylated hydroxyanisole (BHA), or a combination thereof.

* * * * *